United States Patent [19]

Wonn

[11] 4,130,010
[45] Dec. 19, 1978

[54] BUBBLE DETECTOR
[75] Inventor: James W. Wonn, Hempfield Township, Westmoreland County, Pa.
[73] Assignee: Westinghouse Electric Corp., Pittsburgh, Pa.
[21] Appl. No.: 824,593
[22] Filed: Aug. 15, 1977
[51] Int. Cl.² .......................................... G01N 29/02
[52] U.S. Cl. ....................................................... 73/19
[58] Field of Search .................... 73/19, 61 R, 194 A; 55/277; 210/DIG. 22

[56] References Cited

U.S. PATENT DOCUMENTS

| | | | |
|---|---|---|---|
| 2,573,390 | 10/1951 | Blanchard | 73/19 |
| 3,283,562 | 11/1966 | Heisig et al. | 73/19 |
| 3,608,272 | 9/1971 | Di Peri et al. | 55/277 |
| 3,640,271 | 2/1972 | Horton | 73/194 A |
| 3,853,500 | 12/1974 | Gassmann et al. | 55/277 |

OTHER PUBLICATIONS

Nishi; "Ultrasonic Detection of Bubbles with Doppler Flow Transducers", *Ultrasonics,* pp. 173–179, Jul. 1972.

*Primary Examiner*—Stephen A. Kreitman
*Attorney, Agent, or Firm*—D. Schron

[57] ABSTRACT

Apparatus for detecting bubbles in drilling mud so that appropriate corrective action may take place prior to a possible blowout. A low frequency acoustic field is transmitted through the drilling mud which causes the displacement of any bubbles rising through the mud. A high frequency acoustic doppler detection circuit then detects movement of the bubbles in accordance with their displacement by the low frequency field.

9 Claims, 10 Drawing Figures

BUBBLE DETECTOR

BACKGROUND OF THE INVENTION

1. Field of the Invention

The invention in general relates to bubble detection, and particularly to the detection of bubbles in the drilling mud of offshore drilling operations.

2. Description of the Prior Art

In the drilling of an oil or gas well, drilling fluid referred to in the industry as "mud," is pumped into the drill pipe where it proceeds out through the drill bit and up the annular space between the drill pipe and the walls of the hole. The purpose of the circulating mud is to clean, cool and lubricate the bit, flush to the surface the cuttings from the bore hole and to protect the walls of the hole until casing is inserted. The density of the mud is carefully controlled at the surface so as to contain various pressures encountered in the hole.

As a well is drilled into the vicinity of an oil deposit, gases may be released form porous rock and find their way into the circulating mud. The presence of such gas in the mud may modify the buoyancy of the drilling string and can cause extensive damage if it goes undetected. Instances have been recorded where drill pipe has been thrown straight up from the well with consequent extensive damage to the drill rig and other equipment when falling back to earth.

Blowouts have been known to cause disastrous fires, and in many instances the gases released may be noxious, such as hydrogen sulfide.

In offshore drilling, without proper controls, emerging gases may disrupt footings of rigs, causing capsizing, and in other instances floating vessels may actually sink since they cannot float on a layer of bubbles.

Presently, detection of down hole conditions is made by an examination of the circulating mud, at the surface. What is needed, however, is the detection of bubbles at a relatively early stage so as to allow corrective action to be immediately taken.

Several acoustic methods have been proposed for the detection of bubbles; however, not in the field of oil well drilling. For example, one system has been proposed for detecting bubbles from leaking containers having pressurized gas therein. The arrangement immerses the containers to be tested in a liquid and an acoustic doppler system is utilized for projecting acoustic energy into the liquid. The appearance of any bubbles from a leaking container causes a doppler frequency shift, indicative of the leak. Such a system, however, for use in conjunction with an oil well would not operate satisfactorily since the presence of solid particulate matter being carried by the drilling mud would cause a doppler readout, even without the presence of gas bubbles.

SUMMARY OF THE INVENTION

The present invention detects bubbles in a liquid subject to inclusion of solid particles which can scatter acoustic energy and includes a relatively low frequency acoustic generation system which is operable to project acoustic energy into a region of the liquid to insonify it with standing waves. A second system in the form of a relatively higher frequency acoustic motion detection system is operable to detect motion of the bubbles in the region, displaced due to the low frequency insonification.

DESCRIPTION OF THE PREFERRED EMBODIMENT

Figure 1:
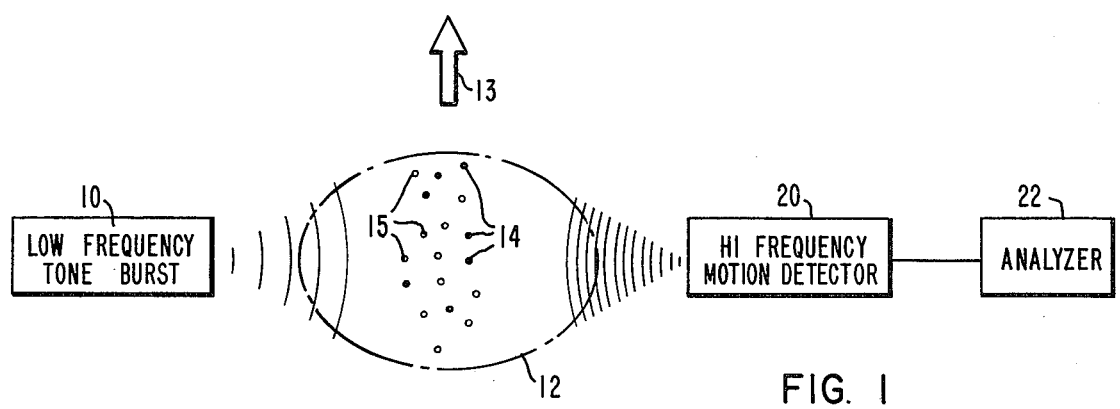
FIG. 1 is a block diagram of the basic concept of the present invention.

In FIG. 1 a low frequency acoustic generation system 10 provides repetitive tone bursts of acoustic energy to insonify a region 12 under investigation. Passing through the region 12 in the direction of arrow 13 is a fluid containing both solid particles 14 shown in black and gas bubbles 15 shown as circles.

By way of example, the frequency of the acoustic wave provided by system 10 may be in the order of 20 kilohertz and when the bubbles 15 are insonified with this tone burst, the many small bubbles agglomerate into fewer large bubbles, and these large bubbles are rapidly displaced to a new location in the field. It is believed that the displacement is due to density gradients in the liquid produced by the 20 kilohertz standing wave field. The low density gas bubbles are especially responsive to such gradient, while the solid particles are not.

A high frequency acoustic motion detection system 20 is provided to detect motion of the bubbles displaced by the low frequency insonification. An analyzer 22 coupled to the motion detection system 20 will then provide an indication of bubble movement toward and away from the detection system 20.

Figure 2:
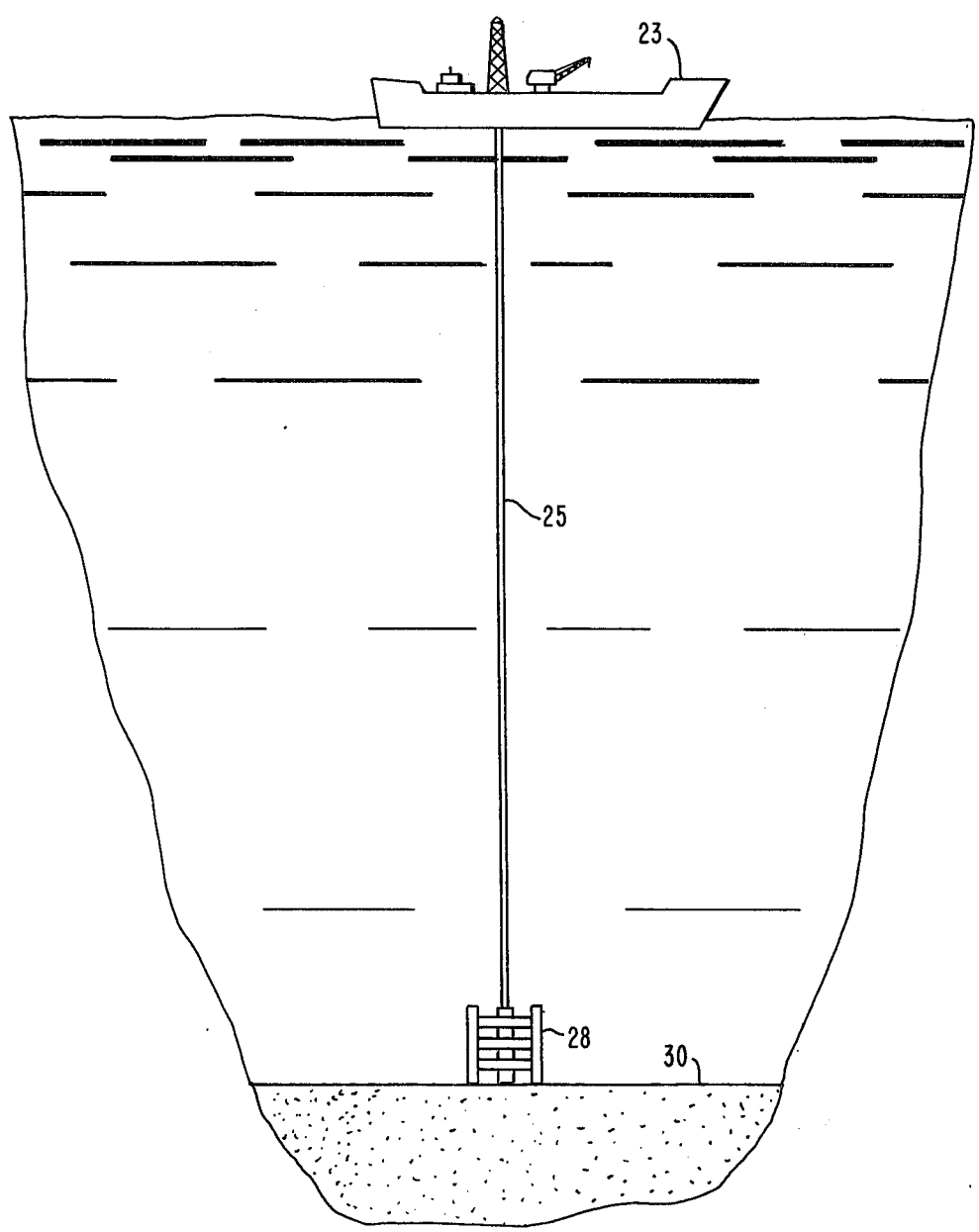
FIG. 2 is a view of an offshore drilling operation.

The principles of the present invention can be utilized in various systems where bubbles are to be detected in the presence of other acoustic scatterers. It will, however, be particularly described with respect to an offshore drilling operation, such as illustrated in FIG. 2. A surface vessel 23 confined on station, such as by anchors and/or acoustic means, has a marine riser 25 extending therefrom to a blowout preventer (BOP) 28 on the bed 30 of a body of water and at the top of a well being drilled.

In order to give advance warning of bubble formation, it would be desirable to place the apparatus of the present invention as close to the drill bit as is possible and practical. One possible location would be at the end of the casing normally used in the drilling operations; however, this would necessitate a plurality of systems, one for each casing. Another might be on the marine riser, just at the top of BOP 28 and coupled to the riser by and any one of a number of well-known techniques to transmit acoustic energy into, and receive reflected energy from, the fluid.

Figure 3:
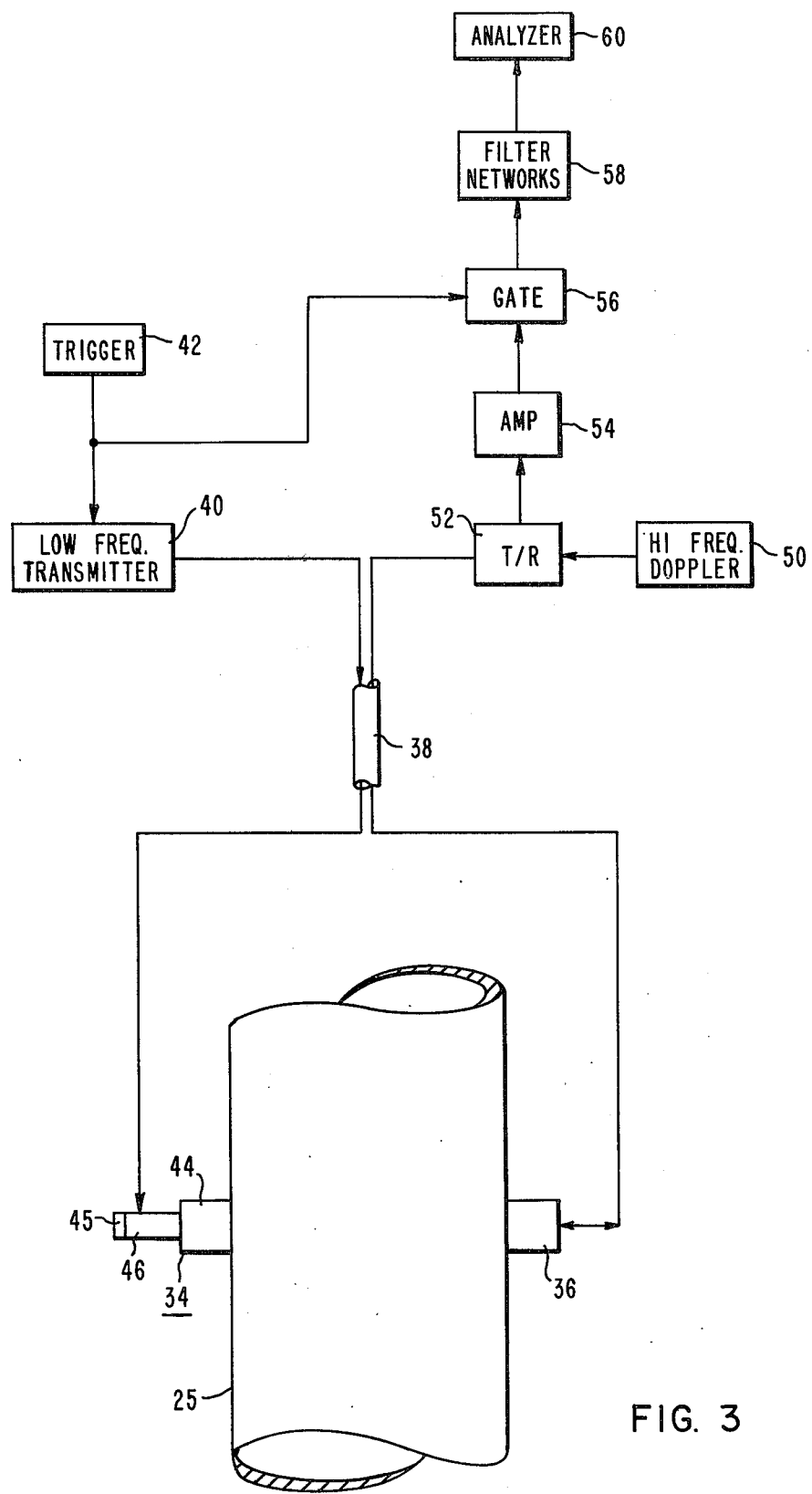
FIG. 3 is a block diagram of one embodiment of the present invention.

FIG. 3 illustrates, by way of example, a transmitter-transducer 34 of the low frequency system and a transmitter/receiver transducer 36 of the high frequency system positioned opposite one another on the marine riser 25 at a position which would be close to the BOP.

By means of a multiconductor cable 38 extending from the transducer location to the surface vessel, signals may be provided to, and conducted from the transducers. The transmitting apparatus which may be aboard the surface vessel includes a low frequency transmitter 40, for example 20 kilohertz, operable to supply transducer 34 with a predetermined number of cycles of 20 kilohertz tone, as governed by the trigger circuit 42. The transmitting transducer 34 may be of a conventional Tonpilz construction which includes a head mass 44, a tail mass 45 and a central motor/generator section 46.

The high frequency motion detection system is conveniently of the doppler type and includes a high frequency, for example 1 megahertz, transmitter 50 operable to supply a signal to transducer 36 by way of transmit/receive (T/R) switch 52. Doppler return signals are conducted from transducer 36 through T/R switch 52 to an amplifier 54 and then through an analog gate circuit 56 which is operable to pass the received signal only when provided with the trigger signal from trigger circuit 42 so that gate 56 is opened to pass signals only when the region under investigation is being insonified. In this manner, the appearance of any doppler shift frequencies is correlated with the repetition rate of the low frequency tone burst to achieve high immunity to background noises.

Various types of detection circuits and readouts could be provided, and FIG. 3 illustrates by way of example the inclusion of filter networks 58 of a predetermined design to just pass certain bands of frequency where doppler shift, due to bubble movement, may be expected.

Various operations may be performed on the filtered signals, such as thresholding and display, recording, or as illustrated in FIG. 3, merely displaying by means of a frequency analyzer 60.

Figure 4:
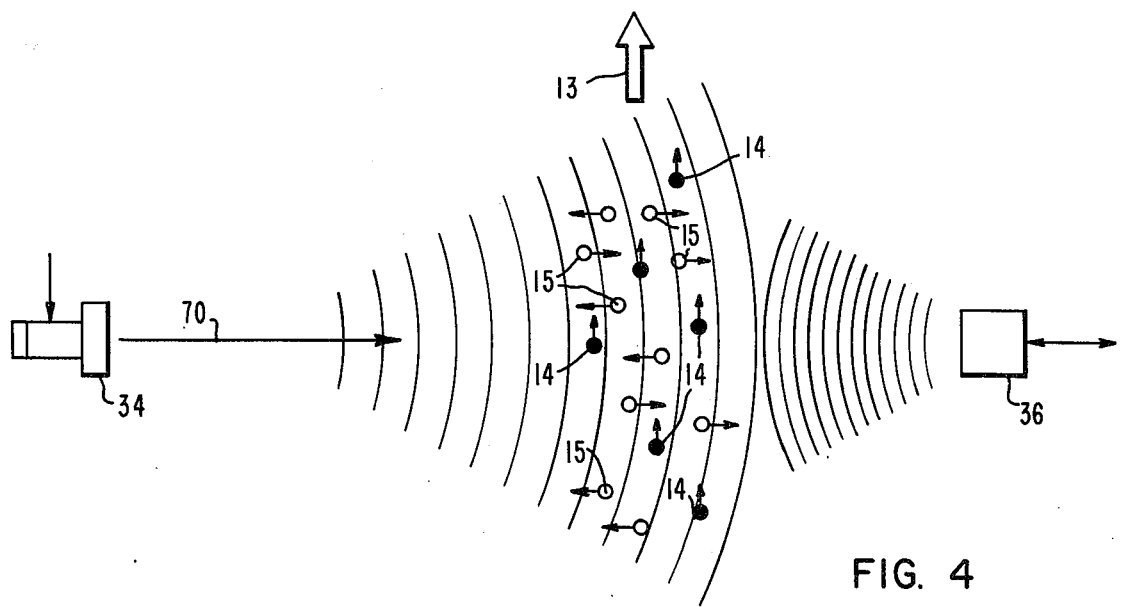
FIG. 4 illustrates the movement of bubbles and particulate matter under the influence of a sound field.

FIG. 4 again illustrates on a larger scale the solid particle 14 and bubbles 15 entrapped in the drilling mud flowing in the direction of arrow 13. The low frequency sound burst is directed toward the region along acoustic axis 70 and, as a result thereof, it is believed that pressure and density gradients are established in the mud. These gradients have no effect on the solid particulate matter; however, the bubbles are especially responsive to such gradient and are displaced from a region of higher pressure and density to one of lower pressure and density. Accordingly, and as illustrated by the arrows on the bubbles, depending upon where the bubbles are in the gradient field, some will move away from the transducer 34 while others will move toward it.

Any relative bubble movement toward and away from doppler transducer 36 will cause a doppler frequency shift output signal indicative, not only of the bubble movement, but also of the relative velocity of the bubble.

Figure 5:
FIG. 5 is the trigger waveform for the transmitter of FIG. 3.
Figure 6A:
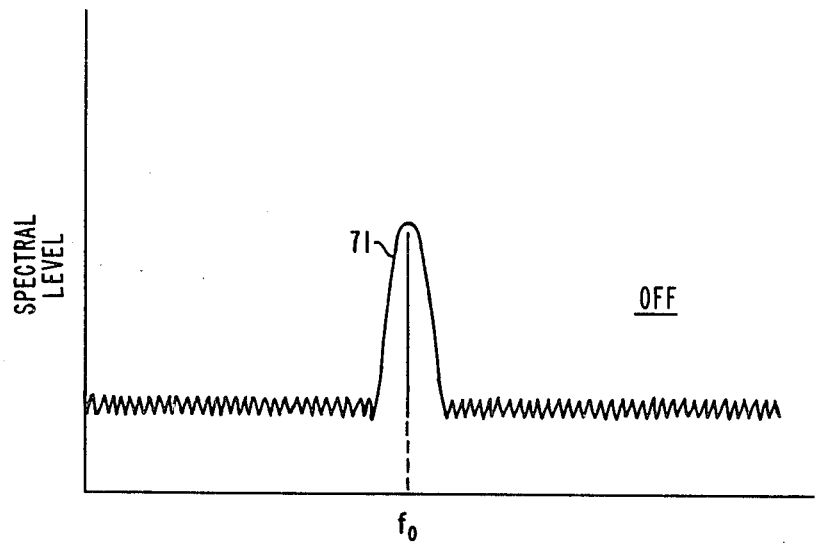
FIGS. 6A and 6B are frequency spectrums of the doppler system of FIG. 3 for off and on conditions of the transmitter.

In operation, movement of the mud with solid particulate matter, past the doppler transducer 36 will provide some doppler shift output frequencies as normal background output. In addition, contributing to this background doppler shift, will be the drill string moving and banging around within the marine riser. The frequency of the insonifying acoustic wave is chosen so as to impart to the bubbles a certain velocity, or range of velocities, which will produce a doppler shift frequency or range of frequencies, and with a relatively high amplitude so as to be distinguishable from the normal background doppler shifts. For example, FIG. 5 illustrates the off and on times of the low frequency transmitter 40 and corresponds to the output signal of trigger circuit 42. FIG. 6A is a curve of spectral level versus frequency and represents the output of doppler transducer 36 when transmitter 40 is in an off condition. It is seen that the waveform includes a relatively high output level at frequency $f_o$, and a statistical distribution 71 of doppler shifted frequency components backscattered from turbulent fluid elements in the acoustic path.

Figure 6B:
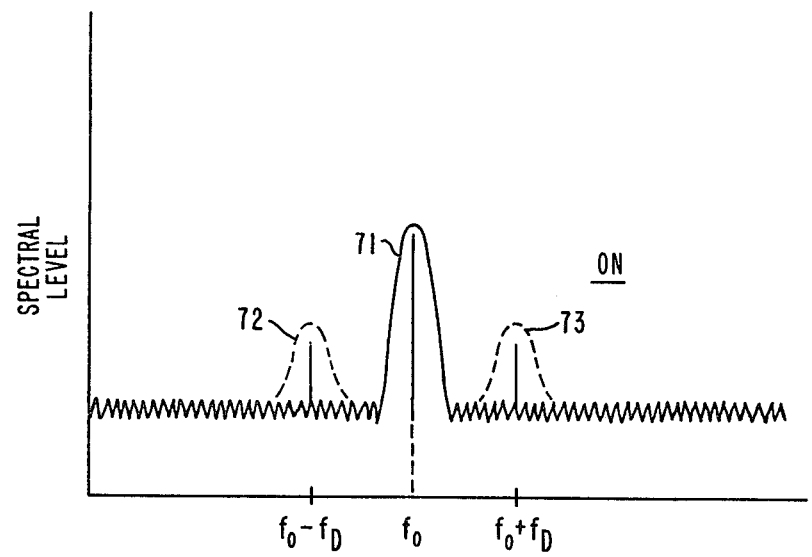

FIG. 6B illustrates the spectral level versus frequency of the doppler transducer 36 for the on period of transmitter 40 and it is seen that in addition to the background signal at $f_o$, there are two other prominent signals appearing at $f_o + f_d$ and $f_o - f_d$, $f_d$ representing the doppler shift due to the previously explained bubble movement toward and away from the doppler transducer. In FIG. 3, the filter networks 58 are designed so as to pass a small range of frequencies centered about $f_o - f_d$ and $f_o + f_d$, as indicated by dotted lines 72 and 73.

Figure 7A:
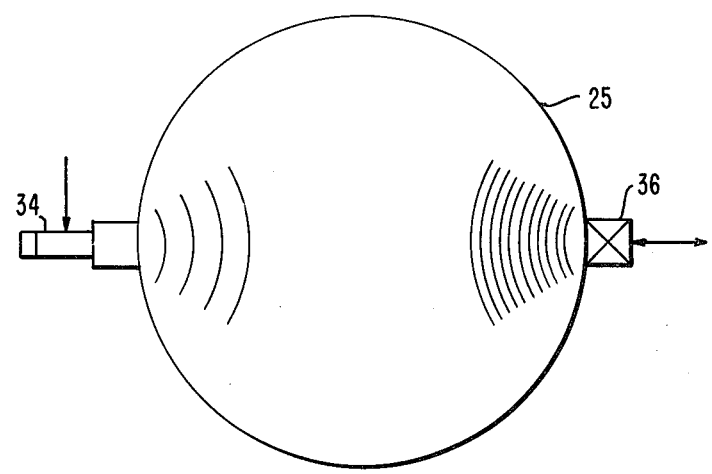
FIGS. 7A and 7B are plan views of two positioning arrangements for the transducers utilized in FIG. 3.
Figure 7B:
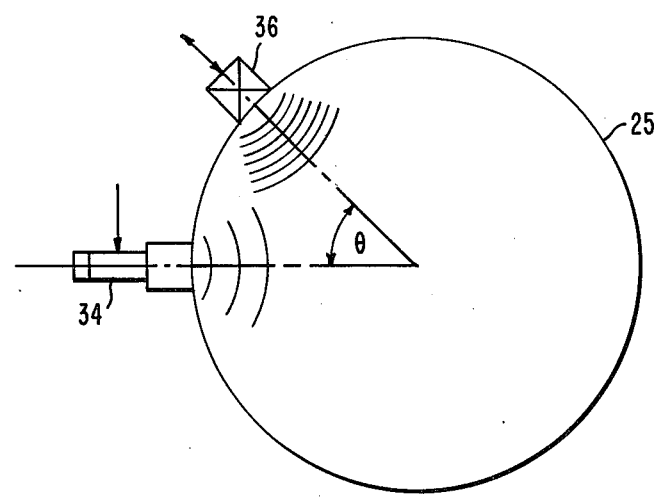

FIG. 7A is a plan view of the apparatus on the marine riser 25 for the situation depicted in FIG. 3. It is seen that transmitter-transducer 34 and transmitter/receiver transducer 36 are diametrically opposed. Various other arrangements are possible, including that illustrated in FIG. 7B wherein the acoustic axes of the two transducers are at a relative angle $\theta$ with respect to one another, where $\theta$ is less than the 180° orientation of FIG. 7A. Other arrangements, such as concentric arrangement of the two transducers or a cordal arrangement of the two transducers are likewise possible.

Figure 8:
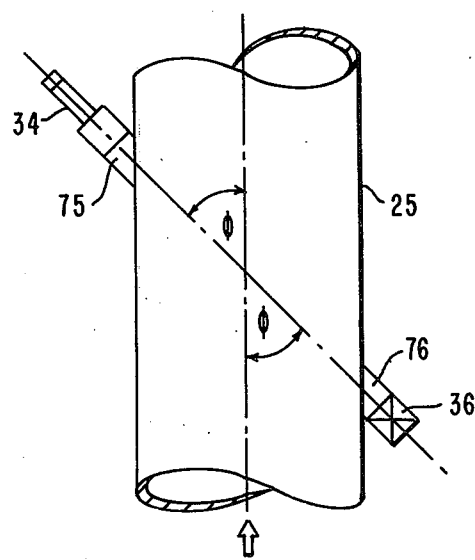
FIG. 8 is a view of an alternate transducer placement for a fluid conducting pipe.

FIG. 3 illustrates the transducers as being on a horizontal plane; however, it is obvious that other orientations are possible. For example, FIG. 8 illustrates the two transducers 34 and 36 at an angle $\theta$ relative to the riser central axis, in which instance suitable couplers or extending bosses 75 and 76 would be provided on the marine riser. With such arrangement a doppler signal due to mud flow would also appear in the frequency distribution curves of FIGS. 6A and 6B and an indication of mud velocity may be obtained.

I claim:

1. Apparatus for detecting bubbles in a liquid subject to inclusion of solid acoustic energy scatterers, comprising:
    (A) a relatively low frequency acoustic generation system operable to project acoustic energy into a region of said liquid to insonify it with standing waves;
    (B) a relatively higher frequency acoustic motion detection system operable to detect motion of bubbles in said region displaced due to said low frequency insonification.

2. Apparatus according to claim 1 wherein
    (A) said liquid is flowing in a pipe; and
    (B) said systems include respective transducers arranged on said pipe.

3. Apparatus according to claim 2 wherein
    (A) said acoustic generation system includes a single transmitter transducer;
    (B) said motion detection system includes a single transmitter/receiver transducer; and
    (C) said transducers are diametrically opposed.

4. Apparatus according to claim 2 wherein
    (A) said acoustic generation system includes a single transmitter transducer;

(B) said motion detection system includes a single transmitter/receiver transducer; and
(C) said transducer have acoustic axes disposed at an angle $\theta$ with respect to one another.

5. Apparatus according to claim 2 wherein
(A) said respective transducers are positioned at different levels on said pipe.

6. Apparatus according to claim 1 wherein
(A) said acoustic generation system includes means for periodically insonifying said region.

7. Apparatus according to claim 6 wherein
(A) said motion detection system is a doppler frequency shift system.

8. Apparatus according to claim 7 which includes:
(A) transducer means;
(B) transmitter means coupled to said transducer means for projecting said relatively higher frequency acoustic signal toward said region; and
(C) detection means coupled to said transducer means for detecting any predetermined doppler shift frequencies.

9. Apparatus according to claim 8 wherein
(A) said detection means includes gating means for passing the signal provided by said transducer means;
(B) filter means for passing only a selected range of transducer means signal; and
(C) said gating means being operated in synchronism with said low frequency periodic insonification.

* * * * *